(12) United States Patent
Murad

(10) Patent No.: US 6,194,452 B1
(45) Date of Patent: *Feb. 27, 2001

(54) STABLE PHARMACEUTICAL COMPOSITIONS INCLUDING ASCORBIC ACID AND METHODS OF USING SAME

(76) Inventor: Howard Murad, 4316 Marina City Dr., Marina del Rey, CA (US) 90292

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/182,180

(22) Filed: Oct. 30, 1998

Related U.S. Application Data

(60) Provisional application No. 60/064,631, filed on Nov. 7, 1997.

(51) Int. Cl.$^7$ .................................................. A61K 31/34
(52) U.S. Cl. ............................................. 514/474; 424/60
(58) Field of Search ......................... 424/59, 401, 280, 424/184, 72, 62; 514/844, 474

(56) References Cited

U.S. PATENT DOCUMENTS

| | | | | |
|---|---|---|---|---|
| 3,873,713 | * | 3/1975 | Haas et al. ............................ | 424/280 |
| 4,122,029 | | 10/1978 | Gee et al. ............................ | 252/309 |
| 4,218,250 | | 8/1980 | Kasprzak ................................. | 106/3 |
| 4,265,878 | | 5/1981 | Keil ........................................ | 424/68 |
| 4,268,499 | | 5/1981 | Keil ........................................ | 424/68 |
| 4,311,695 | | 1/1982 | Starch .................................... | 424/184 |
| 4,720,353 | * | 1/1988 | Bell et al. ............................. | 252/309 |
| 4,818,521 | | 4/1989 | Tamabuchi ............................ | 424/62 |
| 4,853,474 | | 8/1989 | Bahr et al. ............................ | 556/445 |
| 4,938,969 | | 7/1990 | Schinitsky et al. ................... | 424/642 |
| 5,136,068 | | 8/1992 | Bahr et al. ............................ | 556/445 |
| 5,140,043 | | 8/1992 | Darr et al. ............................ | 514/474 |
| 5,290,605 | * | 3/1994 | Shapira ................................ | 424/439 |
| 5,455,035 | * | 10/1995 | Guerrero et al. ..................... | 424/401 |
| 5,545,399 | * | 8/1996 | Lee et al. ............................. | 424/59 |
| 5,574,063 | | 11/1996 | Perricone ............................. | 514/474 |
| 5,587,149 | * | 12/1996 | Punto et al. ........................... | 424/59 |
| 5,609,854 | * | 3/1997 | Guerrero et al. ..................... | 424/59 |
| 5,629,004 | * | 5/1997 | Candau et al. ........................ | 424/401 |
| 5,656,280 | * | 8/1997 | Herb et al. ........................... | 424/401 |
| 5,780,676 | * | 7/1998 | Boehm et al. ........................ | 562/490 |
| 5,804,203 | * | 9/1998 | Hahn et al. ........................... | 424/401 |
| 5,811,083 | * | 9/1998 | Pelle et al. ............................ | 424/59 |
| 5,843,411 | | 12/1998 | Hernandez et al. ................... | 424/59 |
| 5,853,741 | * | 12/1998 | Znaiden et al. ...................... | 424/401 |
| 5,935,559 | * | 8/1999 | Afriat et al. .......................... | 424/70.12 |

OTHER PUBLICATIONS

Murray et al., "Harper's Biochemistry Twenty-fourth Edition," Appleton & Lange, 1996, pp. 612–613.
Dahms, G.H. and Zombeck, A., "New Formulation Possibilities Offered by Silicone Copolyols," *Cosmetics and Toiletries*, vol. 110, No. 3, 91–96, 1995.
Padh, H. "Vitamin C: New Insights into its Biochemical Functions," *Nutr. Rev.*, vol. 49, No. 49, No. 3, 65–70, 1991.
Hameyer, P. and Gould, C., "Organosilicon without Emulsifiers," *Manufacturing Chemist*, 20–25, Jan. 1990.
DiSapio, A.J. and Frid, P., "Silicon Glycols for Cosmetic and Toiletry Applications," Preprints International Federation Societies Cosmetic Chemists, 15$^{th}$ International Congress, 89–103, Sep. 1988, London.
Friberg, S.E. et al., "Emulsions are not only Two Liquids," *Cosmetics and Toiletries*, vol. 102, 87–98, Feb. 1987.
Wendel, S.R. and DiSapio, A.J., "Organofunctional Silicones for Personal Care Applications," *Cosmetics and Toiletries*, vol. 98, 103–106, May 1983.
DiSapio, A.J. and Starch, M.S., "New Silicon Emulsifier Technology," *Cosmetics and Toiletries*, vol. 6, 55–57, Aug. 1981.

* cited by examiner

*Primary Examiner*—William R. A. Jarvis
*Assistant Examiner*—Vickie Kim
(74) *Attorney, Agent, or Firm*—Pennie & Edmonds LLP

(57) ABSTRACT

The present invention relates to a non-irritating, stable pharmaceutical composition including a solution of at least one pharmaceutically acceptable silicone or oil and a source of pharmaceutically acceptable ascorbic acid, wherein the solution is present in an amount sufficient to inhibit degradation of the ascorbic acid while facilitating the prevention or treatment of skin damage. The present invention also relates to a method for modifying free radical damage to skin by administering the above pharmaceutical composition in a therapeutically effective amount sufficient to treat and/or prevent free radical damage to skin.

24 Claims, No Drawings

STABLE PHARMACEUTICAL COMPOSITIONS INCLUDING ASCORBIC ACID AND METHODS OF USING SAME

CROSS-FEFERENCE TO RELATED APPLICATIOHNS

This application claims priority to Provisional Application Ser. No. 60/064,631, filed Nov. 7, 1997.

TECHNICAL FIELD

This invention relates to non-irritating, stable pharmaceutical compositions including a solution of at least one pharmaceutically acceptable silicone or oil component, and a source of pharmaceutically acceptable ascorbic acid. The invention also relates to a method for treating skin damaged by free radicals which comprises administering the above pharmaceutical composition in a therapeutically effective amount sufficient to treat and/or prevent free radical damage to skin.

BACKGROUND OF THE INVENTION

Ascorbic acid, also known as vitamin C, is an essential vitamin in the human body, which cannot synthesize vitamin C on its own. Although widely recognized for its role in the human immune system, ascorbic acid is also essential to other functions, such as the synthesis of collagen. Ascorbic acid's benefits are largely attributable to its ability to act as a reducing agent. Thus, ascorbic acid is able to boost the immune system by scavenging harmful free radicals, which are highly reactive molecular fragments having one or more unpaired electrons. [N. Sax & R. Lewis Sr., *Hawley's Condensed Chemical Dictionary*, 11th ed. Van Nostrand Reinhold 1987]. These free radicals are typically generated by the production or transfer of energy; thus, organs that use, or are exposed to, a great deal of energy, such as the brain and skin, generate numerous free radicals. For example, the transfer of energy from ultraviolet light to the skin generates free radicals such as singlet oxygen, superoxide anions, and hydroxyl radicals. [U.S. Pat. No. 5,574,063, Col. 1, lines 33–46]. If unchecked, these free radicals steal ions from other molecules, thereby destroying cells and tissues and causing chain reactions that oxidize lipids, DNA and enzymes. This often results in physical manifestations, such as sunburn and premature aging. [Id. at Col. 1, lines 40–50]. At high concentrations, ascorbic acid can protect the body against free radicals by donating ions to the free radicals, thereby neutralizing them. Moreover, ascorbic acid can help regenerate the reduced form of Vitamin E, α-tocopherol, thereby rejuvenating another one of the body's major antioxidants. [H. Padh, *Vitamin C: Newer Insights into its Biochemical Functions*, Nutr. Rev. 49:65–70 (1991)].

Additionally, ascorbic acid acts as an enzyme or coenzyme in several of the body's internal chemical processes by reducing various chemical components in the process. In particular, ascorbic acid is essential to the formation of collagen, the key structural component of the extracellular network that gives strength and resilience to bodily tissues. Collagen consists of three helices spiraled around each other and bound together by hydrogen bonds, which individually are weak but collectively impart a structural strength greater than steel upon the collagen. The hydrogen bonds are catalyzed through the action of two enzymes, hydroxylase and lysyl oxidase, which are activated by ascorbic acid. Without ascorbic acid, the hydrogen bonds will not form and the collagen will fall apart, which results in a deterioration of the structural fabric of the skin, wrinkles, and in extreme cases resulting in scurvy. Ascorbic acid is not only essential to the body's production of collagen, but in the production of epinephrin, bile acid and steroids as well. [Murray et al., *Harper's Biochemistry Twenty-Fourth Edition*, Appleton & Lange, pgs. 612–613. (1996)].

Unfortunately, the same attributes that make ascorbic acid vital to the human body also make it susceptible to rapid degradation, thereby making it difficult to formulate stable pharmaceutical compositions with therapeutically effective amounts of ascorbic acid. The rapid degradation of ascorbic acid is largely due to: stereochemical strains created by polar repulsive forces, oxidative degradation due to the propensity of ascorbate anions to act as a reductant, and degradation due to bulk water attack. [U.S. Pat. No. 5,140,043, Col. 2, lines 24–47].

Previously, efforts were made to overcome these difficulties by using low weight ascorbic acid, nonaqueous solvents, or derivatives of ascorbic acid. All of these methods limit the bioavailability of ascorbic acid and therefore limit the effectiveness of the formulation.

In particular, U.S. Pat. No. 5,140,043 discloses allegedly stable ascorbic acid compositions. These compositions consist of aqueous solutions containing a concentration of L-ascorbic acid above 1% W/V and having a pH below 3.5. The acidic pH of the topical application could irritate the user's skin, making the application less desirable.

Thus, a need exists for non-irritating, stable pharmaceutical compositions of ascorbic acid, which may also be used for the prevention or treatment of skin damage caused by the harmful effects of free radicals.

SUMMARY OF THE INVENTION

The present invention relates to a non-irritating, stable pharmaceutical composition which includes a solution of at least one pharmaceutically acceptable silicone component including one or more silicones or oils, and a source of pharmaceutically acceptable ascorbic acid, wherein the solution is present in an amount sufficient to inhibit degradation of the ascorbic acid while facilitating the prevention or treatment of skin damage.

In one embodiment, the silicone component includes a silicone having a general formula of $[(CH_3)_2SiO]_x$, wherein x is an integer from about 3 to 12. In an alternate embodiment, the silicone component includes a silicone having a general formula of $(CH_3)_3SiO\{(CH_3)_2SiO\}_y Si(CH_3)_3$, wherein y is an integer from about 0 to 10. In a preferred embodiment the silicone component is selected from the group of oil, cyclomethicone, dimethicone, and a mixture thereof. The solution is present in about 5 to 90 weight percent of the pharmaceutical composition.

In another embodiment, the silicone component includes an emulsifier of at least one silicone copolyol. Preferably, the emulsifier is cyclomethicone copolyol. Furthermore, the emulsifier is present in about 2 to 10 weight percent of the pharmaceutical composition.

In yet another embodiment, the source of ascorbic acid is a pharmaceutical ascorbic salt or ester of ascorbic acid. Preferably, the source of ascorbic acid is L-ascorbic acid. The source of ascorbic acid is present in about 1 to 60 weight percent of the pharmaceutical composition. In a preferred embodiment, the ascorbic acid is present in about 5 to 25 weight percent of the pharmaceutical composition.

In another embodiment, the pharmaceutical composition further includes an aqueous carrier. In a preferred embodiment, the aqueous carrier is present in about 25 to 50 percent of the pharmaceutical composition. In another preferred embodiment, the substantially all of the source of ascorbic acid is dispersed within the aqueous carrier. In another preferred embodiment, the pharmaceutical composition further includes at least one of a glucosamine, an amino acid, or a mixture thereof, dispersed within the aqueous carrier.

In a preferred embodiment, the pharmaceutical composition also includes an ingredient complex of at least one of a vitamin $B_{12}$ source, a carotenoid, a vitamin A source, and a pilewort extract. Preferably, the vitamin $B_{12}$ source is cyanocobalamin, the carotenoid is beta carotene, and the vitamin A source is retinyl palmitate. In another embodiment, the vitamin $B_{12}$ source is present in about 0.0001 to 0.1 weight percent, the carotenoid is present in about 0.01 to 5 weight percent, the vitamin A source is present in about 0.01 to 5 weight percent, and the pilewort extract is present in about 0.01 to 3 weight percent of the pharmaceutical composition.

Alternatively, the pharmaceutical composition may also include at least one of a vitamin source, antioxidant, skin conditioner, cosmetic additives, and emulsion modifiers. In a preferred embodiment, the vitamin source is a vitamin E source, the antioxidant is a catechin-based preparation, and the emulsion modifier is an electrolyte. The vitamin source is typically present in about 0.05 to 10 weight percent, and the emulsion modifier is typically present in about 0.1 to 2 weight percent of the pharmaceutical composition.

In a further embodiment, the invention relates to a method for modifying free radical damage to skin by administering the above pharmaceutical composition in a therapeutically effective amount sufficient to modify, i.e., prevent, treat, etc., free radical damage to skin. Preferably, the pharmaceutical composition is administered topically, although oral and other routes of administration are also suitable.

In yet another embodiment, the composition may be administered concurrently with, and/or subsequently to, at least one additional pharmaceutical composition that is also used to treat and/or prevent free radical damaged to the skin or enhances the efficacy of the composition disclosed herein.

In one embodiment, the topical application used for treatment of free radical damaged skin includes about 0.001 g to 10 g of ascorbic acid. In a preferred embodiment, the topical application includes about 0.05 g to 5 g of ascorbic acid, and in a more preferred embodiment about 0.7 g to 1.3 g of ascorbic acid is included.

DETAILED DESCRIPTION OF THE INVENTION

The present invention relates to non-irritating, stable pharmaceutical compositions of ascorbic acid for the prevention and/or treatment of skin damage caused by free radicals, as well as methods for modifying free radical-type skin damage by administering the pharmaceutical composition in a therapeutically effective amount sufficient to modify free radical damage to skin. The pharmaceutical composition is made of a solution that includes a silicone component including at least one silicone or oil, and a source of ascorbic acid. The composition may contain various additional components, such as emulsifiers including at least one silicone copolyol in the solution, an aqueous carrier phase, and at least one glucosamine or amino acid. The source of ascorbic acid may be contained within the aqueous carrier phase. The compositions of the present invention are essentially free of irritancy, preferably completely free of irritancy. Without wishing to be bound by any particular theory, Applicant believes the compositions of the present invention have reduced irritancy or are non-irritating due in part to the silicon formulation. Typically the compositions of the present invention have less than 50% water, preferably less than 35% water, more preferably the compositions are substantially anhydrous, and most preferably the compositions are completely anhydrous.

The present invention is believed to increase the stability of ascorbic acid by creating an anhydrous barrier around the source of ascorbic acid to reduce its exposure to air and external moisture. The present invention provides ascorbic acid in a form that assures its efficacy in preventing and treating dermatological disorders and cosmetic conditions caused by ultraviolet light or natural aging. The present compositions also provide the ascorbic acid source a prolonged stability and storage life. Formulations according to the present invention may be administered to effectively prevent, inhibit or reduce the formation and/or the intensity of wrinkles, the roughness and dryness of skin, and the skin pigmentation caused by overexposure to ultraviolet radiation. Furthermore, the silicone permits the ascorbic acid to be dispersed therein and is readily absorbed through the skin when applied topically. Preferably, the ascorbic source is uniformly dispersed in the silicone component.

The solution includes a silicone component including at least one silicone or oil. One or more silicones are the preferred compounds for the solution, since they are non-reactive and have relatively low surface tensions for the solution. These properties advantageously permit the silicone component to create a barrier coating around the source of ascorbic acid, thus reducing its exposure to air and moisture, minimizing the rate of oxidation, and thereby increasing the stability of the ascorbic acid source. Even upon application to a patient in need, the silicone will continue to coat the source of ascorbic acid and protect it by inhibiting oxidation. If this occurs and the efficacy of the ascorbic acid source is decreased, an oil-in-water emulsifier may be added as discussed below to overcome this potential difficulty. Pharmaceutically acceptable silicones include organosiloxane fluids, preferably methylsiloxane fluids. The organosiloxanes include cyclopolysiloxanes having a general formula $[(CH_3)_2SiO]_x$ and linear siloxanes having a general formula $(CH_3)_3SiO\{(CH_3)_2SiO\}_ySi(CH_3)_3$, where x is an integer from 3 to 12, preferably 4 to 10, and more preferably 5 to 8, and y is an integer from 0 to 10, preferably 0 to 8, and more preferably 0 to 6. In particular, cyclomethicone and dimethicone may be used in the present invention. Also, other thicker silicones preferred herein include silica or other polymers, such as the octamethylcyclotetrasiloxane, organopolysiloxane, poly(dimethylsiloxane), poly(methylphenylsiloxane), octamethyltrisiloxane, cyclopentasiloxane, polysilicone, and the like. Alternatively, pharmaceutically acceptable oils may be used for the solution to provide suitable anhydrous barriers for the source of ascorbic acid. Thus, paraffin oils, fatty acid esters of alcohols, triglycerides, parabens, and the like, may also be used for the solution. Moreover, a combination of the silicones and pharmaceutically acceptable oils may be used to form the solution. The solution is present in about 5 to 90 weight percent, preferably about 15 to 80 weight percent, and more preferably, about 25 to 75 weight percent of the pharmaceutical composition.

Various silicones have a low viscosity and low reactivity, which makes them ideal for coating the source of ascorbic acid but renders them relatively insoluble in aqueous solutions. Thus, an emulsifier may be added to increase the solubility of the silicone to facilitate combination with certain sources of ascorbic acid. A suitable emulsifier may be generated by combining the silicone with one or more highly water soluble polyoxylated substituents, thereby creating a structure known as a silicone copolyol. These silicone copolyols function similarly to traditional organic emulsifiers by anchoring themselves at the water/oil phase boundary—in the water phase by a hydrophilic polyether fraction and in the oil phase by a lipophilic alkyl group. Unlike various hydrocarbon-based emulsifiers, the silicone copolyols possess a highly flexible siloxane backbone between these two anchor groups, thereby allowing the siloxane backbone to adapt to interface geometries without creating stearic hindrances. Thus, these emulsifiers facilitate creation of more stable, visco-elastic films at the water/oil interface. Preferably, the silicone copolyols are dimethicone and cyclomethicone copolyols. Also, various combinations of the emulsifiers are contemplated by the present invention. Alternatively, if pharmaceutically acceptable oils are used in the continuous phase, then silicone copolyols having lipophilic alkyl moieties, such as cetyl dimethicone and laurylmethicone copolyols, are preferred. These emulsifiers may be present in about 2 to 10 weight percent, preferably about 2.5 to 8 weight percent, more preferably about 3 to 6 weight percent of the present pharmaceutical composition.

The source of ascorbic acid contained within the solution is preferably L-ascorbic acid, although other forms of ascorbic acid are also suitable for the present invention. The ascorbic acid source may also be pharmaceutically acceptable salts or esters of ascorbic acid, such as ascorbyl palmitate, dipalmitate L-ascorbate, sodium L-ascorbate-2-sulfate, or an ascorbic salt, such as sodium, potassium, and calcium, or mixtures thereof. When used, the preferred salt is calcium ascorbate. When topical or oral formulations of the present pharmaceutical composition are used, it is preferred that a non-acidic form of ascorbic acid be used to reduce the skin or stomach irritation that may occur when using an acidic form. The source of ascorbic acid is present in a therapeutically effective amount, typically at least about 1 to 60 weight percent of the pharmaceutical composition. The ascorbic acid is preferably present in about 1 to 50 weight percent, and more preferably in about 5 to 25 weight percent of the composition.

Ascorbic acid is water soluble and therefore in certain applications it may be advantageous to use an aqueous carrier to increase the bioavailability of ascorbic acid and aid in the absorption of ascorbic acid. The present invention overcomes the difficulties posed by the degradation of ascorbic acid source due to bulk water attack by generating an emulsion in which the aqueous carrier is the dispersed phase. Thus, the source of ascorbic acid is contained within smaller isolated aqueous particles reducing the risk of degradation due to bulk water attack. The risk of degradation is also minimized through the use of deionized or distilled water. Other forms of water may be used provided that the water or contaminants contained therein do not affect the stability of the ascorbic acid source. The aqueous carrier, when used, is present in about 20 to 60 weight percent, preferably about 25 to 50 weight percent, and more preferably about 30 to 45 weight percent the pharmaceutical composition. Thus, the ascorbic acid may be dispersed in the silicone component, in an optional aqueous carrier, or partially in both the silicone component and the optional aqueous carrier. When the aqueous carrier is present, it is preferred that substantially all of the source of ascorbic acid is dispersed within the aqueous carrier. The aqueous carrier generally tends to form an emulsion or suspension in the silicone component. The pharmaceutical composition also preferably includes at least one of a glucosamine, an amino acid, or a mixture thereof, dispersed within the aqueous carrier when it is present. Thus, one preferred embodiment is a silicone component, and an ascorbic acid source and at least one glucosamine and amino acid dispersed within an aqueous carrier.

In another preferred embodiment, an ingredient complex of at least one source of vitamin $B_{12}$, carotenoid, source of vitamin A, and pilewort extract is included within the present pharmaceutical composition. More preferably, all four ingredients are present in the complex. This complex may be present in addition to, or without, the preferred embodiment having a silicone component, and an ascorbic acid source and at least one glucosamine or amino acid, or a mixture thereof, dispersed within an aqueous carrier. The ingredient complex may be used to provide additional antioxidants and the skin soothing properties of pilewort extract, to enhance the efficacy of the present ascorbic acid composition. Moreover, the antioxidants present in the ingredient complex, which are subject to the same degrading forces as ascorbic acid, are also shielded from oxygen and moisture by the silicone component coating the ascorbic acid source.

Vitamin A facilitates healthy skin cell growth and tissue formation facilitates by inhibiting the production of excess skin cells that eventually flake off and tend to clog pores. The vitamin A source, when used, is typically vitamin A complexed to an acetate or palmitate, and preferably is retinyl palmitate. The vitamin A source may be present in about 0.01 to 5 weight percent, preferably in about 0.02 to 3 weight percent, more preferably in about 0.03 to 2 weight percent of the composition. Vitamin A is toxic at high levels, such that if vitamin A is taken in doses of more than 50,000 IU per day over a period of several months it can produce toxic effects in adults.

The carotenoid component that may be used in the ingredient complex includes at least one powerful antioxidant, such as beta-carotene, canthaxanthin, zeaxanthin, lycopen, lutein, crocetin, and capsanthin. Beta-carotene is a carotenoid that is predominantly found in the skin. Beta-carotene protects the integrity of skin cell structure, helps the body modify various skin conditions, and enhances the immune system. Carotenoids, preferably beta-carotene, may be present in about 0.01 to 5 weight percent, preferably about 0.02 to 4 weight percent, and more preferably about 0.03 to 3 weight percent of the pharmaceutical composition.

A source of vitamin $B_{12}$ is also contained within the complex. Vitamin $B_{12}$ is a water soluble vitamin that is extremely effective at small doses. It aids in the formation and regeneration of red blood cells; the proper utilization of fats, carbohydrates, and proteins; and the maintenance of a healthy nervous system. Vitamin $B_{12}$ also works synergistically with all of the other B vitamins, as well as Vitamins A, E, and C. The vitamin $B_{12}$ source is a cobalamin, preferably cyanocobalamin. The vitamin $B_{12}$ source may be present in about 0.0001 to 0.1 weight percent, preferably about 0.0005 to 0.05 weight percent, and more preferably about 0.001 to 0.01 weight percent of the composition.

Pilewort, whose scientific name is *Ranunculus Ficaria*, improves the physical appearance of skin by soothing and softening the skin. The active ingredients in pilewort extract are believed to be saponins, phenolic compounds, and glycosides of flavone derivatives. Pilewort extract may be present in about 0.01 to 3 weight percent, preferably about 0.05 to 2 weight percent, and more preferably about 0.1 to 1 weight percent of the pharmaceutical composition.

Furthermore, functional additives can be added to the pharmaceutical composition quite easily. These additives may be used with any of the embodiments or preferred embodiments disclosed herein. The additive is typically included in the composition by mixing it into the appropriate phase before the emulsion is made. Polar additives can be dissolved in the aqueous carrier, while non-polar additives are mixed in the solution. Functional additives contemplated by the present invention are vitamins, antioxidants, skin conditioners, cosmetic additives, modifiers, and other additives known to those skilled in the art.

First, the therapeutic effect of the present invention may be enhanced through the addition of vitamins to the pharmaceutical composition, or through concurrent or subsequent administration. In particular, those vitamins known to have a beneficial effect upon the skin may be incorporated into the appropriate phase of the present invention. For example, fat soluble vitamins such as vitamin E, which retards cellular aging, vitamin A, which maintains proper growth of skin cells, and vitamin D, which aids in the assimilation of vitamin A, may be incorporated into the solution. Additionally, water soluble vitamins such as the various vitamin B complexes, which aid in the maintenance of healthy skin, may be incorporated into the aqueous carrier. The vitamins and/or their derivatives are incorporated into the present invention in therapeutically effective amounts. The vitamins may be present in about 0.05 to 10 weight percent, preferably about 1 to 5 weight percent of the pharmaceutical composition.

Antioxidants may also be incorporated into the present pharmaceutical compositions as functional additives. Powerful antioxidants, such as bioflavinoids, catechin-based preparations such as proanthanol and proanthocyanidin, and the like, may be incorporated into the present invention in therapeutically effective amounts.

Furthermore, skin conditioning components can also be incorporated into the present pharmaceutical composition as the functional additive. Examples of suitable skin conditioning components are moisturizers, such as glycerol, and emollients known to those skilled in the art of pharmaceuticals and cosmetics. These skin conditioning components may be incorporated in amounts sufficient to soften and soothe the skin, which are readily determinable by one of ordinary skill in the art.

Additionally, one or more cosmetic additives may be incorporated into the pharmaceutical compositions as a functional additive. When used, cosmetic bases such as propylene glycol and polyethylene glycol may be present in about 1 to 30 weight percent of the pharmaceutical composition. Fragrances and perfumes such as essential oils extracted from a wide variety of flowers, leaves, fruit, roots, and wood; animal scents such as musk and ambergris; resinous extracts such as terpenes and balsams; and synthetic fragrances may also be incorporated. The perfumes may be present in about 0.05 to 1 weight percent of the pharmaceutical composition. Moreover, perfume fixatives such as squalane may be incorporated into the present pharmaceutical compositions in about 0.1 to 1 weight percent of the pharmaceutical composition. Additionally, preservatives (such as methylparaben), pigments (such as titanium dioxide), and other similar functional additives known to those skilled within the art, may also be incorporated.

Furthermore, when the pharmaceutical composition is an emulsion it may be stabilized or modified through the use of emulsion modifiers such as organic co-emulsifiers, co-solvents for both phases, electrolytes, and other additives known to those skilled in the art. An oil-in-water emulsifier, for example, may be included in the present pharmaceutical composition to overcome the encapsulating effects of the silicone and silicone copolyols. In small amounts, oil-in-water emulsifiers will not disrupt the bulk emulsion, but they will increase the volatility of the thin silicone film when the pharmaceutical composition is applied to a person's skin. The use of small amounts of oil-in-water emulsifiers facilitates closer contact of the ascorbic acid with the skin, which improves the efficacy of the pharmaceutical compositions. Electrolytes, such as chlorides of alkalis and alkaline earths, and sulfates of sodium, potassium, and magnesium, are particularly good at stabilizing emulsions. Additionally, agents such as moisturizers and water soluble UV filters that exhibit electrolytic behavior also exhibit the same stabilizing effect. These electrolytes may be present in about 0.1 to 2 weight percent of the pharmaceutical composition.

The pharmaceutical compositions of the present invention are generally made by first combining and mixing the ingredients for the solution, i.e., at least one pharmaceutically acceptable oil and/or silicone, the silicone copolyol, and any fat soluble functional additives. At the same time, the ingredients for the aqueous carrier, e.g., deionized water and the source of ascorbic acid, are mixed, as well. When both phases are uniformly mixed, the aqueous carrier is slowly added to the continuous phase while mixing at high speed. The emulsion is typically then mixed for about thirty minutes to one hour. Afterwards, the emulsion is preferably homogenized.

Furthermore, the viscosity of the pharmaceutical composition may be adjusted by varying the aqueous carrier content of the emulsion when an emulsion is present. The greater the water content of the emulsion, the greater its viscosity. Thus, if a lotion is desired, less water should be included within the emulsion; whereas if a thick cream is desired, more water should be used. The specific amount of water used for the emulsion is readily determinable by one of ordinary skill in the art. Additionally, the viscosity of the emulsion is inversely proportionate to the size of the dispersed aqueous particles, i.e., the smaller the particle, the greater the emulsion viscosity. Thus, if more viscous pharmaceutical compositions are desired, the emulsion should be homogenized or mixed faster for longer periods of time to generate small aqueous particles.

The magnitude of a prophylactic or therapeutic dose of the composition to modify free radical damage to skin will vary with the sensitivity of the patient's skin and the route of administration. The dose, and perhaps the dose frequency, may also vary according to the age, body weight, and response of the individual patient. Generally, about 1 ml to 14 ml, preferably about 3 ml to 10 ml, of the pharmaceutical composition may be applied as a topical application when used on a person's face and neck. Those skilled in the art will recognize that more of the pharmaceutical composition may be needed to treat addition portions of a person's body. The pharmaceutical composition is usually applied 1 to 6 times daily, preferably 1 to 4 times daily, and more preferably 1 to 2 times daily. In general, the total daily dose range of active ingredients, for the conditions described herein, is from about 0.001 g to 20 g. The unit dose range should be from about 0.001 g to 10 g, preferably about 0.05 g to 5 g, and more preferably about 0.7 g to 1.3 g. In a preferred form, the compositions are used to treat skin damaged by free radicals. The formulation of the present invention may be used alone or in conjunction with other skin treatments.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with the individual patient's response.

The term "substantially anhydrous" as used herein means less than 10 percent water, preferably less than 5 percent water, and most preferably less than 2 percent water. The terms "therapeutically effective amount of the composition" or "therapeutically effective amount of the pharmaceutically acceptable salt thereof" are encompassed by the above-described frequency and dosage amounts. The term "modify", as used herein to describe the effect of the composition on free radical damaged skin, includes preventing, treating, and conditioning the skin, as well as facilitating the effects of ascorbic acid. As used herein, the term "substantially" typically means greater than about 75 weight percent, preferably greater than about 90 weight percent, and more preferably greater than about 98 weight percent.

Although any suitable route of administration may be employed for providing the patient with an effective dosage of the composition according to the methods of the present invention, topical administration is preferred. Other suitable routes of administration include, for example, oral, rectal, parenteral, intravenous, topical, transdermal, subcutaneous, intramuscular, and like forms of administration may be employed. Suitable dosage forms include tablets, troches, dispersions, suspensions, solutions, capsules, patches, suppositories, and the like, although the topical dosage forms are preferred.

The pharmaceutical compositions used in the methods of the present invention include the active ingredients described above, and may also contain pharmaceutically acceptable carriers, excipients and the like, and optionally, other therapeutic ingredients, such as for concurrent or subsequent administration.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumine (N-methylglucamine), and procaine.

The compositions used in the methods of the present invention include preparations such as suspensions, solutions and elixirs; aerosols; or carriers such as starches, sugars, microcrystalline cellulose, diluents, granulating agents, lubricants, binders, disintegrating agents, and the like, in the case of oral solid preparations, such as powders, capsules, and tablets, with the oral solid preparations being preferred over the oral liquid preparations. The most preferred oral solid preparations are tablets and capsules. Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions for use in the methods of the present invention suitable for administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Such compositions may be prepared by any of the methods of pharmacy known to those of ordinary skill in the art, but all methods include the step of bringing into association the carrier with the active ingredient. The compositions may be prepared by uniformly and intimately admixing the active ingredient with liquid carriers or fmely divided solid carriers or both, and then, if necessary, shaping the product into the desired presentation.

For example, a tablet may be prepared by compressing or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

EXAMPLES

The invention is further defined by reference to the following examples, which describe in detail the preparation of the compound and the compositions used in the methods of the present invention, as well as their utility. The examples are representative, and they should not be construed to limit the scope of the invention.

Example 1

Professional Treatment Gel According to the Invention

The professional treatment gel was prepared by first mixing the ingredients of Part A in a main processing tank until uniformly mixed. Part B was then sprinkled into the Part A mixture. Parts A and B were then mixed until completely uniform.

| | TRADE NAME/ SUPPLIER | INGREDIENTS | % BY WEIGHT |
|---|---|---|---|
| Part A | GRANSIL GCM/GRANT INDUSTRIES* | Octamethylcyclotetrasiloxane and Organopolysiloxane | 40 |
| | VITAMIN E ACETATE/ROCHE* | Tocopheryl Acetate | 10 |
| Part B | VITAMIN C ULTRA FINE POWDER/ROCHE | Ascorbic Acid | 50 |

*Are commercially available from Grant Industries Inc., Elmwood Park, NJ; Roche Vitamins Inc., Parsippany, NJ.

The above formula generated a white opaque gel having a viscosity of about 80,000 to 120,000 cps (RVT #6 at 10 rpm and 25° C.).

Example 2

Treatment Gel According to the Invention

In order to form a treatment gel, the ingredients of Part A were mixed in a main processing tank until uniformly mixed. Part B is then sprinkled into the Part A mixture. Parts A and B are then mixed until completely uniform.

| | TRADE NAME/ SUPPLIER | INGREDIENTS | % BY WEIGHT |
|---|---|---|---|
| Part A | GRANSIL GCM/GRANT INDUSTRIES | Octamethylcyclotetrasiloxane and Organopolysiloxane | 79.8 |
| | VITAMIN E ACETATE/ ROCHE | Tocopheryl Acetate | 5 |
| | LIQUAPAR OIL/ISP* | Isopropylparaben and Isobutylparaben and Butylparaben | 0.2 |
| Part B | VITAMIN C ULTRA FINE POWDER/ROCHE | Ascorbic Acid | 15 |

*Are commercially available from ISP Chemicals Inc., Calvert City, KY.

The above formula generated a white opaque gel having a viscosity of about 30,000 to 50,000 cps (RVT #6 at 10 rpm and 25° C.).

Example 3

Second Treatment Gel According to the Invention

The second treatment gel was generated by homogenizing the ingredients of Part A until no gritty feel was observed when it was applied to the skin. Part B was then added and mixed until uniform.

| | TRADE NAME/ SUPPLIER | INGREDIENTS | % BY WEIGHT |
|---|---|---|---|
| Part A | VITAMIN E ACETATE/ROCHE | Tocopheryl Acetate | 2 |
| | DOW CORNING 200 (.65 CS) DOW CORNING* | Dimethicone | 10 |
| | ASCORBIC ACID ULTRA FINE POWDER/ROCHE | Ascorbic Acid | 15 |
| Part B | GRANSIL GCM/GRANT INDUSTRIES | Octamethylcyclotetrasiloxane and Organopolysiloxane | 72.7 |
| | H&R #A11516/77 9701/HAARMANN & REIMER* | Fragrance | 0.05 |
| | GATULINE A/GATTEFOSSE* | Pilewort (Ranunculus Ficaria) Extract | 0.1 |
| | 30% BETA CAROTENE IN VEGETABLE OIL/ROCHE | Beta-Carotene | 0.05 |
| | CYANOCOBALAMIN USP/ROCHE | Cyanocobalamin | 0.001 |
| | VITAMIN E USP-FCC/ROCHE | Tocopherol | 0.05 |
| | VITAMIN A PALMITATE TYPE P1.7/ROCHE | Retinyl Palmitate | 0.05 |

*Are commercially available from Dow Corning Corp., Auburn, MI; Haarmann & Reimer Corp., Teterboro, NJ; Gattefosse Corp., Westwood, NJ.

The above formula generated an opaque light yellow to orange gel having a viscosity of about 10,000 to 20,000 cps (RVT #6 at 10 rpm and 25° C.).

Example 4

Vitamin E and C Gel According to the Invention

A third gel for topical application is created by mixing the Part A ingredients in a main processing tank. In a separate vessel, the ingredients for Part B are premixed until all of the solids are dissolved. Afterwards, Part B is slowly added to Part A while mixing at high speed. The mixing is continued for 30 minutes to one hour until the emulsion is uniform. Once uniformly mixed, the emulsion is homogenized.

| | TRADE NAME/ SUPPLIER | INGREDIENTS | % BY WEIGHT |
|---|---|---|---|
| Part A | ABIL EM97/GOLDSCHMIDT* | Not Available | 2–6 |
| | GE SF 96-5/GE SILICONES | Dimethicone | 15–30 |
| | Vitamin E Acetate/Roche | Tocopheryl Acetate | 0.05–4 |
| Part B | Deionized Water | Water (Aqua) | 31.7 |
| | EPSOM SALT/SPECTRUM* | Magnesium Sulfate | 1 |
| | Ascorbic Acid/Roche | Ascorbic Acid | 0.1–15 |
| | Propylene Glycol | Propylene Glycol | 0.1–30 |
| | GLYDANT PLUS/LONZA* | DMDM Hydantoin and Iodopropynyl Butylcarba-mate | 0.3 |

*Are commercially available from Goldschmidt Cosmetics, Central Islip, NY; GE Silicones, General Electric Company, Waterford, NY; Spectrum Quality Products, Inc., Gardena, CA; Lonza Biologics Inc., Portsmouth, NH.

Topical gels generated using the above formula may have an appearance ranging from an opaque to almost clear gel having a viscosity of about 1,000 to 30,000 cps (RVT #6 at 10 rpm and 25° C.). Suspending 10% of this formulation in water results in a solution having a pH of 3.3.

Example 5

Treatment Gel According to the Invention

A fourth topical gel can be generated by mixing together the ingredients of Part A in a main processing tank. In a separate vessel, Part B is premixed until uniform. In another vessel, the ingredients from Part C are heated to 50° C. until all the solids are dissolved. Part C is then cooled to 30° C. Part C is then added to Part B. The whole solution of Parts B and C are then mixed for 30 minutes to one hour until uniform. Parts B and C are then slowly added to Part A while mixing at high speed. Mixing is continued for 30 minutes to one hour until the entire solution is uniform.

|  | TRADE NAME/ SUPPLIER | INGREDIENTS | % BY WEIGHT |
|---|---|---|---|
| Part A | DOW CORNING 3225 C/DOW CORNING | Cyclomethicone and Dimethicone Copolyol | 3–10 |
|  | GE SF 1204/GE SILICONES | Cyclomethicone | 15–30 |
|  | VITAMIN E ACETATE/ROCHE | Tocopheryl Acetate | 0.05–4 |
|  | PHYTOLANE/BARNET* | Squalane | 0.5 |
|  | #09246M/Shaw Mudge* | Fragrance (Parfum) | 0.1 |
| Part B | Deionized Water | Water (Aqua) | 33.8 |
|  | Ascorbic Acid/Roche | Ascorbic Acid | 0.1–1 |
|  | POTASSIUM PHOSPHATE MONOBASIC/SPECTRUM | Potassium Phosphate | 0.1 |
|  | Propylene Glycol | Propylene Glycol | 0.1–30 |
| Part C | Propylene Glycol | Propylene Glycol | 1 |
|  | Methylparaben | Methylparaben | 2 |

*Are commercially available from Barnet Product Corp., Englewood Cliffs, NJ; Shaw Mudge & Co., Shelton, CT.

The above formula generates an opaque to almost clear gel depending on the specific amounts of ingredients included and having a viscosity of about 1,000 to 30,000 cps (RVT #6 at 10 rpm and 25° C.). Suspending 10% of this formulation in water results in a solution having a pH of 3.3.

Example 6

Treatment Gel Having Glutamic Acid

A fifth topical gel can be generated by mixing together ingredients within the ranges listed in Part A in a main processing tank. In a separate vessel, the ingredients within the ranges listed of Part B is premixed until uniform. In another vessel, the ingredients from Part C are heated to 50° C. until all the solids are dissolved. Part C is then cooled to 30° C. and added to Part B. The whole solution of Parts B and C are then mixed for 30 minutes to one hour until uniform. Parts B and C are then slowly added to Part A while mixing at high speed. Mixing is continued for 30 minutes to one hour until the entire solution is uniform.

|  | TRADE NAME/ SUPPLIER | INGREDIENTS | % BY WEIGHT |
|---|---|---|---|
| Part A | DOW CORNING 3225C/DOW CORNING | Cyclomethicone and Dimethicone Copolyol | 3.0–10.0 |
|  | GE SF 1204/GE SILICONES | Cyclomethicone | 15.0–30.0 |
|  | VITAMIN E ACETATE/ROCHE | Tocopheryl Acetate | 0.05–4.0 |
|  | PHYTOLANE/BARNET | Squalane | 0.5 |
|  | #09246/Shaw Mudge | Fragrance (Parfum) | 0.10 |
| Part B | Deionized Water | Water | 33.8 |
|  | ASCORBIC ACID/ROCHE | Ascorbic Acid | 0.1–15.0 |
|  | POTASSIUM PHOSPHATE MONOBASIC/SPECTRUM | Potassium Phosphate | 0.1 |
|  | GLYCINE/W. R. GRACE* | Glycine | 0.1–1.0 |
|  | L-GLUTAMIC ACID/SPECTRUM | L-Glutamic Acid | 0.1–1.0 |
|  | ASCORBYL GLUCOSEAMINE/COLLABORATIVE LABS* | Chitosan Ascorbate | 0.1–10.0 |
|  | Propylene Glycol | Propylene Glycol | 0.1–30.0 |
| Part C | Propylene Glycol | Propylene Glycol | 1.0 |
|  | Methylparaben | Methylparaben | 0.2 |

*Are commercially available from W. R. Grace & Co., Baton Rouge, LA; Collaborative Laboratories Inc., Stony Brook, NY.

The above formula generates an opaque to almost clear gel depending on the specific amounts of ingredients included having a viscosity of about 1,000 to 30,000 cps (RVT #5 at 10 rpm and 25° C.). Suspending 10% of this formulation in water results in a solution having a pH of 3.2.

Example 7

Treatment Gel Having Glutamic Acid

A sixth topical gel can be generated by homogenizing the ingredients of Part A until no gritty feel is apparent upon application to the skin. Part B ingredients are added by mixing until uniform.

|  | TRADE NAME/ SUPPLIER | INGREDIENTS | % BY WEIGHT |
|---|---|---|---|
| Part A | VITAMIN E ACETATE/ROCHE | Tocopheryl Acetate | 2.0 |
|  | DOW CORNING 200 (.65 CS)/DOW CORNING | Dimethicone | 10.0 |
|  | ASCORBIC ACID ULTRA FINE POWDER/ROCHE | Ascorbic acid | 15.0 |
|  | L-GLUTAMIC ACID, F.C.C./SPECTRUM | Glutamic Acid | 0.5 |
|  | GLYCINE/GRACE | Glycine | 1.0 |
| Part B | GRANSIL GCM/GRANT INDUSTRIES | Cyclopentasiloxane and Polysilicone - 11 | 71.2 |
|  | H&R #A11516/779701/HAARMANN & REIMER | Fragrance | 0.05 |
|  | GATULINE A/GATTEFOSSE | Pilewort (Ranunculus Ficaria) Extract | 0.1 |
|  | 30% BETA CAROTENE IN VEGETABLE OIL/ROCHE | Beta-Carotene | 0.05 |
|  | CYANOCOBALAMIN, USP/ROCHE | Cyanocobalamin | 0.001 |
|  | VITAMIN E, USP-FCC/ROCHE | Tocopherol | 0.05 |

-continued

| TRADE NAME/ SUPPLIER | INGREDIENTS | % BY WEIGHT |
|---|---|---|
| VITAMIN A PALMITATE TYPE P1.7/ROCHE | Ascorbyl Palmitate | 0.05 |

The above formula generates an opaque light yellow to orange gel having a viscosity of about 10,000 to 20,000 cps (RVT #6 at 10 rpm and 25° C.).

Example 8

Treatment Gel According to the Invention

Another topical gel was generated by mixing Part A ingredients in the main processing tank until uniform. Pre-mixed Part B ingredients were added to Part A and mixed until uniform. Part C was premixed until uniform and then Part C was added to the batch and mixed until uniform. Part D ingredients were added and mixed until uniform. Separately, Part E was ground through a 200-mesh screen and then added to the batch. The batch was homogenized while cooling to ensure that the batch temperature did not exceed 40° C. The batch was mixed until completely smooth and grit free.

| | TRADE NAME/ SUPPLIER | INGREDIENTS | % BY WEIGHT |
|---|---|---|---|
| Part A | GRANSIL GCM-5/GRANT INDUSTRIES | Cyclomethicone and Polysilicone 11 | 71.8 |
| | VITAMIN A Palmitate, TYPE P1.7/ROCHE | Retinyl Palmitate | 1 |
| Part B | 30% BETA CAROTENE IN VEGETABLE OIL/ROCHE | Hydrogenated Vegetable oil and Beta-Carotene | 0.05 |
| | SAFFLOWER OIL, HIGH OLEIC/ARISTA* | Safflower (Carthamus Tinctorius) Oil | 0.25 |
| Part C | VITAMIN B12/ROCHE | Cyanocobalamin | 0.05 |
| | EMERESSENCE 1160/HENKEL* | Phenoxyethanol | 0.25 |
| Part D | VITAMIN E ACETATE/ROCHE | Tocopheryl Acetate | 5 |
| | DOW CORNING 200, 0.65 CS./DOW CORNING | Dimethicone | 10.5 |
| | ASCORBIC ACID, ULTRA FINE POWDER, USP-FCC/ROCHE | Ascorbic Acid | 10 |
| | GATULINE A/GATTEFOSSE | Pilewort (Ranunculus Ficaria) Extract | 0.5 |
| Part E | GLYCINE, USP-NF/HAMPSHIRE* | Glycine | 0.5 |

*Are commercially available from Arista Industries Inc, Saint Petersburg, FL; Henkel Corporation, Hoboken, NJ; Hampshire Chemical Corp., Lexington, MA.

The above gel is an off-white, opaque, semi-viscous lotion having a viscosity of about 15,000 cps to 19,000 cps (RVT #5 at 10 rpm at 25° C.).

Examples 9–13

Testing of a Treatment Gel

The treatment gel of Example 8 was administered to 15 female subjects to evaluate the effects on overall appearance of the skin including the effects on the presence of fine lines and wrinkles, skin smoothness and clarity, elasticity of the skin, and moisturization of the skin. A one week conditioning period was used prior to initiation of the study, where subjects were instructed to wash their entire facial area, the neck and neckline at least once a day with a non-moisturizing soap. During the conditioning period and subsequent phases of the study subjects were not allowed to use any moisturizer, sunscreen or liquid make-up. Subjects were also instructed to avoid excessive UV (sunlight) exposure and to avoid tanning salons. Subjects were permitted to use their regular eye and lip products but were not allowed to introduce any new cosmetic product during the study.

After the seven day conditioning period baseline measurements of each test subject was taken. The following measurements and assessments were made of the facial areas: Image analysis using silflo-replicas on both sides of the periorbital area, three Ballistometer readings on one side of the periorbital area, three Cutometer readings on one side of the periorbital area, three Corneometer measurements on one side of the periorbital area, photographs of the left and right eye areas and a frontal view, superficial facial lines based on the Packman and Gans system, and skin clarity assessed from clinical photographs.

Following the baseline measurements, each subject was instructed to apply the treatment gel under supervision and to wait fifteen minutes. Measurements were then repeated as above. Subjects were given the treatment gel and instructed to use the treatment gel twice daily and to record the dates and times of use in a Daily Diary. Daily Diaries were reviewed to assess study compliance. Measurements were repeated at 24 hours, and at two, four and six weeks as described above. Before measurements were taken, all subjects were allowed to acclimate at approximately 71° F. and 26% humidity for 30 minutes.

A total of twelve subjects completed the study. Two subjects discontinued the study for reasons unrelated to product use and one discontinued use due to an adverse reaction.

Example 9

Image Analysis

The texture of the skin, fine lines and wrinkles were assessed by taking negative impressions, or Silflo replicas, of the periorbital area (crows feet) at each test time using Siflo™ impression material and Replica™ locating rings (CuDerm Corporation, Dallas Tex.). These negative impressions, or Silflo replicas, were illuminated at a precisely defined angle of 35° to create shadows that are analyzed according to shades of gray. The skin topography is defined by the: (a) total number of wrinkles; (b) total area of wrinkles; (c) total length of wrinkles; (d) mean length of wrinkles; and (e) mean depth of wrinkles. A wrinkle is defined as any facial line with depths varying from 0 to 300 microns and is classified by its length, depth and area. Fine lines are included as a subset of wrinkles and are defined as having depths of 0 to 60 microns. A percent reduction in the number of wrinkles and fine lines resulting from treatment was calculated.

Table I, below, summarizes the data for wrinkles and fine lines. As indicated in Table I below, there were improvements in wrinkles and fine lines as a result of using the treatment gel for six weeks.

TABLE I

Number of Wrinkles and Fine Lines

| | Baseline | 15 minutes | 24 hours | 2 weeks | 4 weeks | 6 weeks |
|---|---|---|---|---|---|---|
| Number of Wrinkles | | | | | | |
| Mean | 59 | 57 | 57 | 62 | 56 | 54 |
| Mean % Difference from Baseline | | 3% | 6% | 7% | −9% | −9% |
| Number of Fine Lines | | | | | | |
| Mean | 34 | 38 | 38 | 37 | 35 | 32 |
| Mean % Difference from Baseline | | 20% | 13% | 7% | −7% | −6% |

Example 9 indicates that there were improvements in the number of fine lines and wrinkles after use of the treatment gel, prepared by the formulation of Example 8, for six weeks. These changes evidenced a trend towards a reduction in the number of lines and wrinkles after using the product for six weeks.

Example 10

Ballistometer

The Ballistometer (IDRA™, Third Party Research & Development, New York) is an instrument designed to evaluate in vivo, in a non-invasive manner, the viscoelastic properties of the skin. It analyzes the bounce pattern displayed by a probe as it impacts the skin. The kinetic energy of the probe striking the skin is stored by the elastic components of the skin and is then released, causing the probe to rebound. Since the skin is a viscoelastic, anisotropic material, the height that the probe will rebound depends on the amount of stored energy lost in the viscosity of the skin. Thus, the Ballistometer measures the capacity of the skin to absorb mechanical energy and it assesses mostly the behavior of the tissues underlying the stratum corneum. However, the contribution of the stratum corneum cannot be entirely ignored and it is unclear exactly, which layer, or layers, of the skin are involved in the propagation of the impact wave that is generated when the probe impacts the skin. Any effects from treatment, which take some time to manifest result from an alteration of the mechanical properties of the dermis. The density and geometry of the network of collagen fibers controls the mechanical properties of the dermis layers. Changes in skin properties that are due to alteration of the stratum corneum would be observed more quickly, due to the rapid turnover of cells in the epidermis.

Tests with the Ballistometer were conducted by taking three readings on one side of the face in the periorbital area. The height of the first rebound and the coefficient of restitution were measured. The coefficient of restitution is the ratio of the first to the second rebound. Table II, below, summarizes the data for the height of the first rebound and for the coefficient of restitution.

TABLE II

Ballistometer Readings

| | Baseline | 15 minutes | 24 hours | 2 weeks | 4 weeks | 6 weeks |
|---|---|---|---|---|---|---|
| Height of First Rebound | | | | | | |
| Mean | 6.51 | 6.33 | 6.48 | 5.97 | 6.02 | 6.00 |
| Mean % Difference from Baseline | | −3% | 0% | −9% | −8% | −8% |
| Coefficient of Restitution | | | | | | |
| Mean | 0.31 | 0.31 | 0.31 | 0.30 | 0.30 | 0.31 |
| Mean % Difference from Baseline | | −1% | 1% | −1% | −3% | 0% |

The Ballistometer data in Table II shows that there was a reduction in the height of the first rebound. The reduction in the height of the first rebound was interpreted as the skin becoming softer in the lower layers of the skin after using the treatment gel for six weeks.

Example 11

Cutometer

The Cutometer is a commercially available instrument (SEM-575, Courage and Khazaka, Germany) designed to measure the mechanical properties of the skin in a non-invasive manner. It measures the vertical deformation of the skin surface as it is pulled by vacuum suction (500 mm Hg) through the small aperture (2 mm) of a probe. The depth of penetration of the skin into the probe is measured optically with an accuracy of 0.01 mm. The probe is attached to a computer which controls its operation and plots skin deformation as a function of time. From this curve a number of variables can be extrapolated to estimate the elastic, viscoelastic and purely viscous behavior of the skin.

The following parameters were recorded: (a) the immediate distension ($U_e$), measured at 0.1 seconds, (b) the delayed distension ($U_v$); (c) the final distension ($U_f$), measured at 10 seconds; and (d) immediate retraction ($U_r$). The deformation parameters are extrinsic parameters dependent on skin thickness and a variety of important ratios were calculated: (a) $U_r/U_e$, the biological elasticity of the skin, or measurement of the ability of the skin to regain its initial configuration after deformation; (b) $U_v/U_e$, the ratio between the delayed and the immediate deformation, i.e. is viscoelastic to elastic ratio, where an increase in this ratio indicates that there has been an increase in the viscoelastic portion of the deformation and/or a relative decrease of the elastic portion; and (c) $U_r/U_f$, a measure of net elasticity of the skin.

Tests were conducted using the Cutometer by make three measurements on one side of the face on the periorbital area. Table III, below, provides data from the Cutometer readings for the seven parameters discussed above.

TABLE III

Cutometer Readings

| | Baseline | 15 minutes | 24 hours | 2 weeks | 4 weeks | 6 weeks |
|---|---|---|---|---|---|---|
| $U_f$ | | | | | | |
| Mean | 0.148 | 0.157 | 0.128 | 0.185 | 0.118 | 0.105 |
| Mean % Difference from Baseline | | 9% | −8% | 38% | −15% | −23% |

TABLE III-continued

Cutometer Readings

| | Baseline | 15 minutes | 24 hours | 2 weeks | 4 weeks | 6 weeks |
|---|---|---|---|---|---|---|
| $U_e$ | | | | | | |
| Mean | 0.115 | 0.127 | 0.100 | 0.152 | 0.094 | 0.084 |
| Mean % Difference from Baseline | | 15% | −6% | 47% | −13% | −20% |
| $U_v$ | | | | | | |
| Mean | 0.033 | 0.030 | 0.028 | 0.033 | 0.024 | 0.020 |
| Mean % Difference from Baseline | | −5% | −12% | 10% | −23% | −32% |
| $U_r$ | | | | | | |
| Mean | 0.034 | 0.048 | 0.038 | 0.069 | 0.048 | 0.036 |
| Mean % Difference from Baseline | | 46% | 18% | 112% | 40% | 5% |
| $U_r/U_e$ | | | | | | |
| Mean | 0.345 | 0.416 | 0.410 | 0.443 | 0.473 | 0.436 |
| Mean % Difference from Baseline | | 22% | 21% | 30% | 40% | 30% |
| $U_v/U_e$ | | | | | | |
| Mean | 0.285 | 0.243 | 0.270 | 0.236 | 0.273 | 0.267 |
| Mean % Difference from Baseline | | −8% | −2% | −14% | −3% | 3% |
| $U_r/U_f$ | | | | | | |
| Mean | 0.273 | 0.340 | 0.330 | 0.373 | 0.383 | 0.350 |
| Mean % Difference from Baseline | | 26% | 24% | 39% | 42% | 31% |

The data in Table III shows that there were beneficial changes in some of the parameters measured by the Cutometer. The changes in these parameters indicate that the elasticity of the skin increased during treatment with gel prepared by the formulation of Example 8. Most noticeably, the net elasticity and biological elasticity of the skin increased. An increase in these parameters indicates a reversed trend from that found typically in aging skin.

Example 12

Corneometer

The general appearance of soft, smooth skin depends largely on the presence of an adequate amount of water in the stratum corneum. Lack of moisture in the stratum corneum results in degradation of its mechanical properties and the appearance of dry skin. Changes in skin hydration were measured with a Corneometer which is a commercially available instrument (CM-820, Courage and Khazaka Germany) designed to measure changes in the capacitance of the skin resulting from changes in the degree of hydration. It is particularly sensitive to low hydration levels. The Corneometer expresses the capacitance of the skin in arbitrary unit of skin hydration (H). Changes in moisture content of the stratum corneum occur rapidly. These changes are brought about by changes in the environment, including changes in the microclimate of the skin, resulting from the use of hydrating or moisturizing agents or humectants thus, the measurements with the Cutometer indicate changes in deeper layers of the skin, rather than the superficial stratum corneum.

Tests using the Cutometer were conducted by taking 3 measurements on one side of the face in the periorbital area. Table IV, below, provides data for skin hydration (H).

TABLE IV

Corneometer Readings

| | Baseline | 15 minutes | 24 hours | 2 weeks | 4 weeks | 6 weeks |
|---|---|---|---|---|---|---|
| Skin Hydration (H) | | | | | | |
| Mean | 47 | 43 | 47 | 47 | 42 | 46 |
| Mean % Difference from Baseline | | −10% | 1% | 0% | −13% | −3% |

The data in Table IV indicate that the treatment gel prepared by the formulation of Example 8 did not significantly affect skin moisturization after six weeks of use.

Example 13

Photographic Evaluation

Photographs of subjects were taken at designated visits using the Canfield Clinical System of imaging equipment. This particular system permits comparison of photographs to be made with the confidence that the only factors which may have changed are those resulting from treatment. This is achieved by precisely and reproducibly positioning the head of the subject and carefully controlling the lighting, film type and processing. Photographs were taken of the left and right eye areas and a frontal view. Photographs were visually assessed and evaluated by a trained technician before and after use of the treatment gel. Photographs were evaluated for degree of aging, photodamage, fine lines and wrinkles. The following scoring scale was used for visual assessment of the skin:

0=no evidence of aging, photodamage, fine lines and/or wrinkles

1=mild aging, photodamage, fine lines and/or wrinkles 1.5–2.0=moderate aging, photodamage, fine lines and/or wrinkles 2.5–3.0=severe aging, photodamage, fine lines and/or wrinkles Table V, below, provides data for the visual assessment.

Table V: Photographic Evaluation

TABLE V

Photographic Evaluation

| | Baseline | 15 minutes | 24 hours | 2 weeks | 4 weeks | 6 weeks |
|---|---|---|---|---|---|---|
| Visual Assessment Scores | | | | | | |
| Mean | 1.7 | 1.5 | 1.6 | 1.6 | 1.4 | 1.4 |
| Mean % Difference from Baseline | | −13% | −6% | −3% | −15% | −19% |

The data in Table V indicates that there were significant improvements in the condition of the skin after at least 4 weeks of treatment with the treatment gel.

Example 14

Superficial Facial Lines

Superficial facial lines (SFL) were evaluated using the method of Packman and Gans. The method involves rating facial lines for frequency and depth in four component areas of each side of the face before and after use of the test material and multiplying the frequency and depth values to get a score. The assessment scores from the right and left sides of the face are totaled for each side. The right total score and the left total score are averaged, and the percentage reduction in the number of SFLs resulting from treatment is calculated. Table VI, provides data for the number of SFLs.

TABLE VI

Superficial Facial Lines

| | Baseline | 15 minutes | 24 hours | 2 weeks | 4 weeks | 6 weeks |
|---|---|---|---|---|---|---|
| | | Number of Superficial Facial Lines | | | | |
| Mean | 42 | 41 | 41 | 41 | 41 | 40 |
| Mean % Difference from Baseline | | 0% | −1% | −1% | −1% | −3% |

The data in Table VI indicate that there was a significant three percent reduction in SFLs after six weeks of using the treatment gel prepared by the formulation of Example 8.

Example 15

Skin Clarity Grading

The skin clarity of each subject was evaluated visually using a scale ranging from 1 to 5. A score of 5 represents no blemishes and a score of 1 indicates that more than seventy six percent of the skin area has blemishes. The scale decreases by increments of twenty five percent as indicated below:

5=no blemishes
4=1%–25% blemishes
3=26%–50% blemishes
2=51%–75% blemishes
1=76%–100% blemishes An overall full facial score is assigned to each subject at each time point. The score is assessed from the clinical photographs. Table VII provides data for Skin Clarity Grading.

TABLE VII

Skin Clarity Grading.

| | Baseline | 15 minutes | 24 hours | 2 weeks | 4 weeks | 6 weeks |
|---|---|---|---|---|---|---|
| | | Skin Clarity Grading | | | | |
| Mean | 4 | 4 | 4 | 4 | 5 | 5 |
| Mean % Difference from Baseline | | 0% | −2% | 5% | 15% | 12% |

The data in Table VII show that there was a significant improvement in skin clarity after four weeks and six weeks of using the treatment gel prepared by the formulation of Example 8.

Although preferred embodiments of the invention have been described in the foregoing Detailed Description of the Invention, it will be understood that the invention is not limited to the embodiments disclosed but is capable of numerous modifications without departing from the spirit and scope of the present invention. It will be understood that the chemical details may be slightly different or modified by one of ordinary skill in the art without departing from the methods and compositions disclosed and taught by the present invention.

What is claimed is:

1. A non-irritating, stable pharmaceutical composition comprising:

a silicone component of a solution of a combination of at least one linear silicone compound having a general formula of $(CH_3)_3SiO\{(CH_3)_2SiO\}_ySi(CH_3)_3$, wherein y is an integer from about 0 to 10, and at least one cyclopolysiloxane having a general formula $[(CH_3)_2SiO]_x$, wherein x is an integer from 3 to 12, as the sole silicone component of the composition; and a source of pharmaceutically acceptable ascorbic acid dispersed in the silicone component, wherein the solution is present in an amount sufficient to inhibit degradation of the ascorbic acid while facilitating the prevention or treatment of skin damage, wherein the pharmaceutical composition is substantially anhydrous.

2. The pharmaceutical composition of claim 1, wherein the linear silicone compound comprises dimethicone and the cyclopolysiloxane compound comprises cyclomethicone, cyclopentasiloxane, or both.

3. The pharmaceutical composition of claim 1, wherein the solution is present in about 5 to 90 weight percent of the pharmaceutical composition.

4. The pharmaceutical composition of claim 1, wherein the solution further comprises an emulsifier of at least one silicone copolyol.

5. The pharmaceutical composition of claim 4, wherein the emulsifier is present in about 2 to 10 weight percent of the pharmaceutical composition.

6. The pharmaceutical composition of claim 1, wherein the source of ascorbic acid comprises a pharmaceutical salt or ester of ascorbic acid.

7. The pharmaceutical composition of claim 1, wherein the source of ascorbic acid is L-ascorbic acid.

8. The pharmaceutical composition of claim 1, wherein the source of ascorbic acid is present in about 1 to 60 weight percent of the pharmaceutical composition.

9. The pharmaceutical composition of claim 1, wherein the ascorbic acid is present in about 5 to 25 weight percent of the pharmaceutical composition.

10. The pharmaceutical composition of claim 1, wherein the composition further comprises an ingredient complex of a vitamin $B_{12}$ source, a carotenoid, and a pilewort extract.

11. The pharmaceutical composition of claim 10, wherein the vitamin $B_{12}$ source is cyanocobalamin, and the carotenoid is beta carotene.

12. The pharmaceutical composition of claim 10, wherein the vitamin $B_{12}$ source is present in about 0.0001 to 0.1 weight percent, the carotenoid is present in about 0.01 to 5 weight percent and the pilewort extract is present in about 0.01 to 3 weight percent pharmaceutical composition.

13. The pharmaceutical composition of claim 1, wherein the pharmaceutical composition further comprises an antioxidant and at least one functional additive comprising a vitamin source, a skin conditioner, a cosmetic additive, and an emulsion modifier.

14. The pharmaceutical composition of claim 13, wherein the vitamin source comprises a vitamin E source, the antioxidant comprises a catechin-based preparation, and the emulsion modifier comprises an electrolyte.

15. The pharmaceutical composition of claim 13, wherein the vitamin source is about 0.05 to 10 weight percent, and the emulsion modifier is about 0.1 to 2 weight percent, of the pharmaceutical composition.

16. A method for modifying free radical-type skin damage which comprises administering the pharmaceutical composition of claim 1 in a therapeutically effective amount sufficient to modify free radical damage to skin.

17. The method of claim 16, wherein about 0.001 g to 10 g of ascorbic acid is administered topically.

18. The method of claim 16, which further comprises administering in the composition concurrently with at least one additional pharmaceutical composition used to modify free radical damage to the skin.

19. The method of claim 16, which further comprises administering the composition subsequently to at least one additional pharmaceutical composition used to modify free radical damage to the skin.

20. A non-irritating, stable pharmaceutical composition comprising:
    a silicone component of a solution of a combination of at least one linear silicone compound having a general formula of $(CH_3)_3SiO\{(CH_3)_2SiO\}_ySi(CH_3)_3$, wherein y is an integer from about 0 to 10, and at least one cyclopolysiloxane having a general formula $[(CH_3)_2SiO]_x$, wherein x is an integer from 3 to 12, as the sole silicone component of the composition; and
    a source of pharmaceutically acceptable ascorbic acid dispersed in the silicone component, wherein the solution is present in an amount sufficient to inhibit degradation of the ascorbic acid while facilitating the prevention or treatment of skin damage; and
    glucosamine, wherein less than 5 percent water is present in the pharmaceutical composition.

21. A non-irritating, stable pharmaceutical composition comprising:
    a silicone component of a solution of a combination of at least one linear silicone compound having a general formula of $(CH_3)_3SiO\{(CH_3)_2SiO\}_ySi(CH_3)_3$, wherein y is an integer from about 0 to 10, and at least one cyclopolysiloxane having a general formula $[(CH_3)_2SiO]_x$, wherein x is an integer from 3 to 12, as the sole silicone component of the composition; and
    a source of pharmaceutically acceptable ascorbic acid dispersed in the silicone component, wherein the solution is present in an amount sufficient to inhibit degradation of the ascorbic acid while facilitating the prevention or treatment of skin damage;
    a vitamin $B_{12}$ source;
    a carotenoid;
    a vitamin A source; and
    a pilewort extract, wherein the pharmaceutical composition is substantially anhydrous.

22. The pharmaceutical composition of claim 1, wherein less than 5 percent water is present in the pharmaceutical composition.

23. The pharmaceutical composition of claim 22, wherein less than 2 percent water is present in the pharmaceutical composition.

24. The pharmaceutical composition of claim 1, wherein the pharmaceutical composition is completely anhydrous.

* * * * *

UNITED STATES PATENT AND TRADEMARK OFFICE
CERTIFICATE OF CORRECTION

PATENT NO. : 6,194,452 B1
DATED : February 27, 2001
INVENTOR(S) : Howard Murad

It is certified that error appears in the above-identified patent and that said Letters Patent is hereby corrected as shown below:

<u>Column 22,</u>
Line 56 (claim 12, line 5), after "percent" insert -- of the --.

Signed and Sealed this

Twenty-third Day of October, 2001

Attest:

*Attesting Officer*

NICHOLAS P. GODICI
*Acting Director of the United States Patent and Trademark Office*